United States Patent [19]

Seaton

[11] Patent Number: 5,133,342

[45] Date of Patent: Jul. 28, 1992

[54] LEVER TO ALIGN BONES

[76] Inventor: James I. Seaton, 5813 Quintana St., Riverdale, Md. 20737

[21] Appl. No.: 633,951

[22] Filed: Dec. 26, 1990

[51] Int. Cl.$^5$ .............................................. A61F 5/04
[52] U.S. Cl. .......................................... 602/39; 606/54
[58] Field of Search ............... 128/77, 80 R, 84 R, 128/83, 84 C, 88; 606/53–59, 72–74; 254/131, 133 R, 129, 16; 29/271, 278

[56] References Cited

U.S. PATENT DOCUMENTS

| | | | |
|---|---|---|---|
| 3,015,883 | 1/1962 | Brown | 29/271 |
| 3,759,251 | 9/1973 | Adams | 128/69 |
| 3,883,117 | 5/1975 | Powell | 254/131 X |
| 3,945,611 | 3/1976 | Moodie et al. | 254/131 |
| 4,471,768 | 9/1984 | Ciullo | 128/83 |
| 4,482,182 | 11/1984 | Mortensen | 254/131 X |
| 4,708,320 | 11/1987 | Hodges | 254/131 X |
| 4,746,098 | 5/1988 | Abaratin | 254/131 |
| 5,003,969 | 4/1991 | Azer et al. | 606/54 |

Primary Examiner—Robert A. Hafer
Assistant Examiner—Brian E. Hanlon
Attorney, Agent, or Firm—Richard C. Litman

[57] ABSTRACT

A fracture alignment device comprising two clamps adjustably and pivotally mounted on a lever which may be rotated as a second class lever to apply pressure on the bone segments to align the bone segments. The device is both autoclavable and radiolucent, whereby the user may monitor the alignment by means of an X-ray machine, and the device may be used in the operating room.

6 Claims, 2 Drawing Sheets 5,133,342

LEVER TO ALIGN BONES

BACKGROUND OF THE INVENTION

1. Field of the Invention

This invention relates to a fracture alignment device, and more particularly to a second class lever which provides a means for applying an enhanced force upon displaced fractures of the long bones (femur, tibia), allowing for alignment and providing the orthopedic surgeon with a means to maintain fracture reduction while preparing the bone for rigid intramedullary fixation.

2. Description of the Prior Art

Bone aligning and setting devices are known. U.S. Pat. No. 2,110,414 issued to William Bell discloses an arrangement for drawing the fractured bones together after alignment, but does not disclose a means for initially aligning the bones.

U.S. Pat. No. 2,112,447 issued to Joseph O. Peterson discloses a surgical instrument comprising a manually rotated lever having jaws thereon used to break improperly set bones for the purpose of resetting the bones. However, there is no disclosure therein of any structure to align the bones once they have been broken.

U.S. Pat. No. 2,333,033 issued to Leslie E. Mraz discloses a bone splint which uses a complicated arrangement of rack bars and angularly adjustable heads carrying bone prongs to first align and then to bring together bone fragments, the apparatus thereafter serving to hold the bone fragments in place. There is no disclosure therein of a lever means of the type disclosed and claimed herein.

U.S. Pat. No. 2,590,739 issued to Hugo Wagner and Roger Anderson discloses another complicated arrangement for aligning and fixing bone fragments which includes structure pivotally attached to a specifically designed bed. The structure is designed to be connected with the outer end portion of a bone of a patient, such as a humerus, which structure will both mechanically hold and cause desired movement of the bone.

U.S. Pat. No. 2,760,489 issued to Leo J. Hindle discloses an adjustable fracture-setter which relies upon the adjustment of fingers connected to a cylinder to align the bone fragments, the structural elements being constructed of material through which an X-ray beam will pass unobstructed.

U.S. Pat. No. 4,604,997 issued to Giovanni DeBastiani et al. discloses an arrangement specifically designed to align and fix small bones of the hand and feet. The device is not practical for the setting and aligning of long bones such as the femur or tibia.

U.S. Pat. No. 4,628,922 issued to Michael E. Dewar discloses a fracture-reduction apparatus comprising bone anchor pins mounted on pin holders which are slidably and pivotally mounted on a telescopic bar.

U.S. Pat. No. 4,890,631 issued to Jean-Marie Hardy discloses an external fixation device which relies upon bone-engaging pins to hold the bone segments in place.

SUMMARY AND OBJECTS OF THE INVENTION

None of the above-cited references disclose a bone alignment device comprising a lever having semi-cylindrical limb-engaging clamps adjustably and pivotally mounted thereon so as to respectively align two bone segments on opposite sides of the fracture. The clamps are disposed on the lever in such a manner that rotation of the lever about one of the clamps as a fulcrum will serve to move the other clamp in a direction effective to align the bone segments. The lever arm is sufficiently long (twenty-four inches in one embodiment) to deep the surgeon's hands away from direction irradiation from X-ray beams, Thereby reducing the amount and intensity of radiation the surgeon is exposed to. The inventive device is autoclavable and radiolucent, may be used in a sterile field, is lightweight and may be operated by one person. The moving parts require no lubrication and the proximal end is adjustable to fit individual patient leg widths and lengths.

It is an object of this invention to provide a simplified device for the alignment of fractured bone segments.

It is another object of the invention to provide a bone alignment device which is of light weight, economical to manufacture, and which will reduce exposure of the surgeon to radiation.

Other objects, features and advantages of this invention will be apparent from the following detailed description and the appended claims, reference being had to the accompanying drawings forming a part of the specification, wherein like reference numerals designate corresponding parts of the several views.

DETAILED DESCRIPTION OF PREFERRED EMBODIMENTS

Before explaining in detail the present invention, it is to be understood that the invention is not limited in its application to the details of construction and arrangement of parts illustrated in the accompanying drawings, since the invention is capable of other embodiments and of being practiced or carried out in various ways. Also, it is to be understood that the phraseology and terminology employed herein is for the purpose of description and not limitation.

Figure 1:
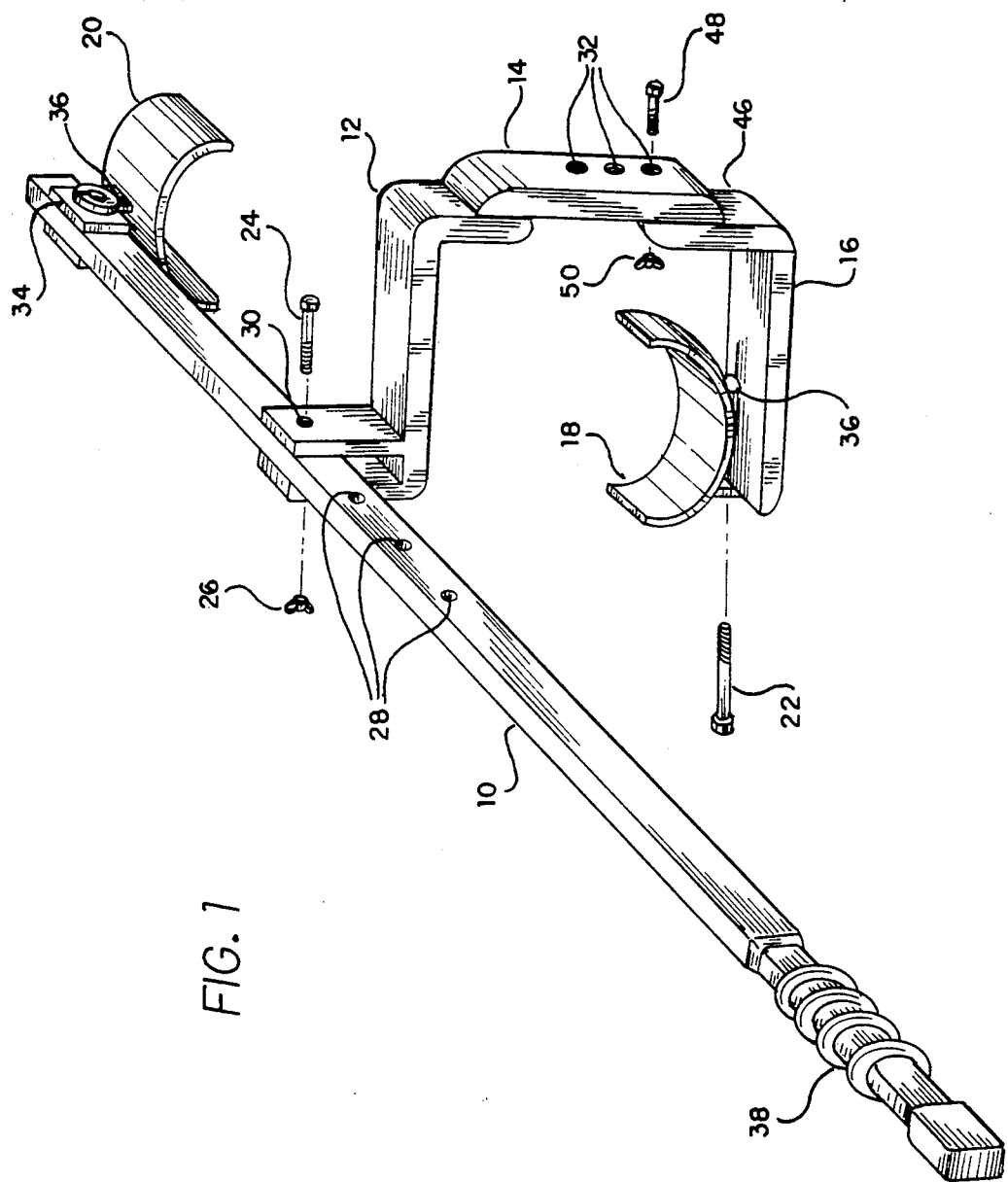
FIG. 1 is a perspective view of the lever for aligning bones showing the adjustable and pivotal mounting of the semicylindrical cups or clamps thereon.

FIG. 1 is a perspective view of the fracture alignment device. Lever 10 has a clamp bracket 12 adjustably attached medially thereto by means of a pivot bolt 24 inserted through hole 30 in bracket 12 and one of a plurality of adjustment holes 28 in lever 10, and held in position by means of a wing nut 26. Clamp bracket 12 has an offset bracket arm 14 integral therewith which has in turn a clamp support bracket 16 adjustably mounted thereon by a screw 48 inserted through one of a plurality of adjustment holes 32 in bracket arm 14 and a hole (not shown) in leg 46 integral with clamp support 16, and tightened by a wing nut 50. Pivotally mounted on clamp support 16 by a hinge means 36 including a pivot bolt 22 is a semicylindrical outer limb clamp 18.

Mounted at one end of lever 10 is a clamp bracket 34 having a semicylindrical inner limb clamp 20 pivotally mounted thereon by hinge means 36. At the opposite end of lever 10 is a handle 38.

Figure 2:
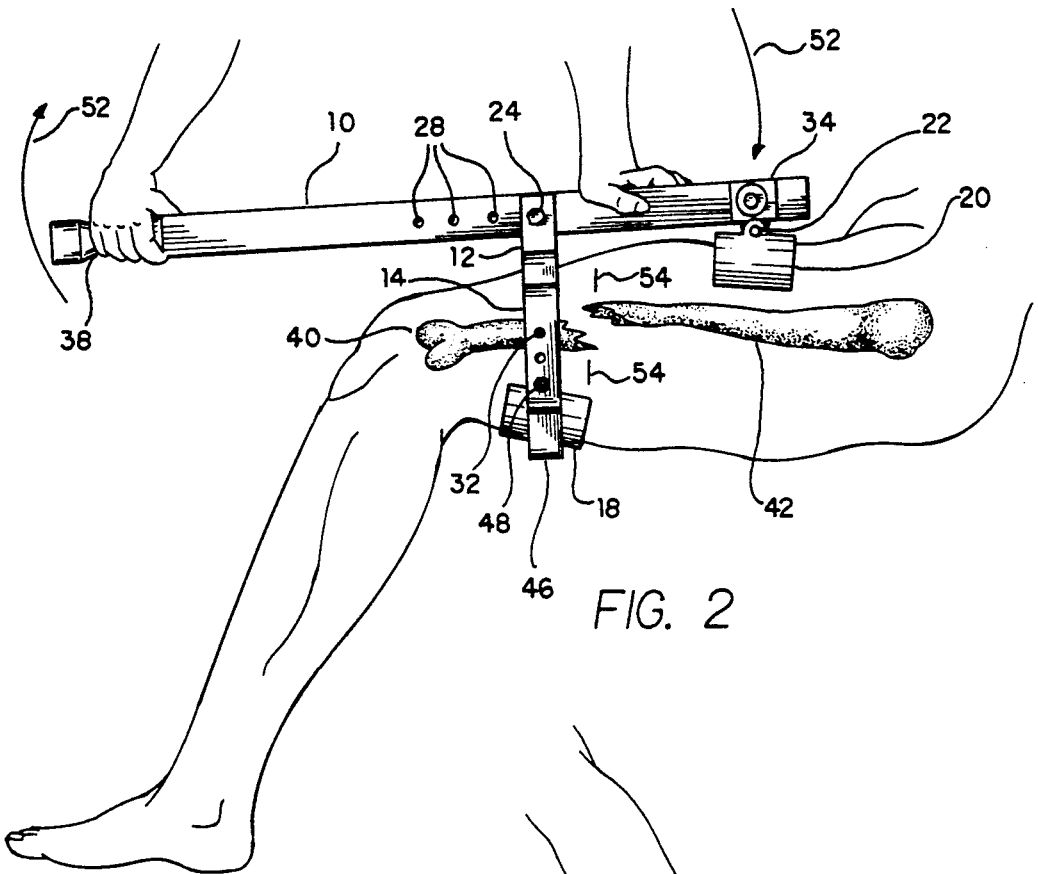
FIG. 2 is a side view showing the lever for aligning bones in use.

FIG. 2 shows how the fracture alignment device is used to align bone segments 40 and 42. Lever 10 functions as a second class lever. As shown in FIG. 2, outer limb clamp 18 is placed so as to cup the injured leg below bone segment 40. Inner leg clamp 20 is located to cup the injured leg above bone segment 42. The user grasps handle 38 with one hand and bears down on lever 10 between pivot bolt 24 and the end of lever 10 having inner limb clamp 20 mounted thereon. By simultaneously exerting an upward pull on handle 38, lever 10 is pivoted clockwise in the direction of arrows 52 in FIG. 2, about pivot bolt 24. Clamps 18 and 20 in turn exert a force o the injured leg to move the fractured ends of bone segments 40 and 42 toward each other in the direction of arrows 54. Because the fracture alignment device is radiolucent, the user is able to monitor the positioning of the fractured ends of the bone segments by means of an X-ray machine, not shown. Once aligned, other means (not shown) may be employed to hold the fractured ends together.

Figure 3:
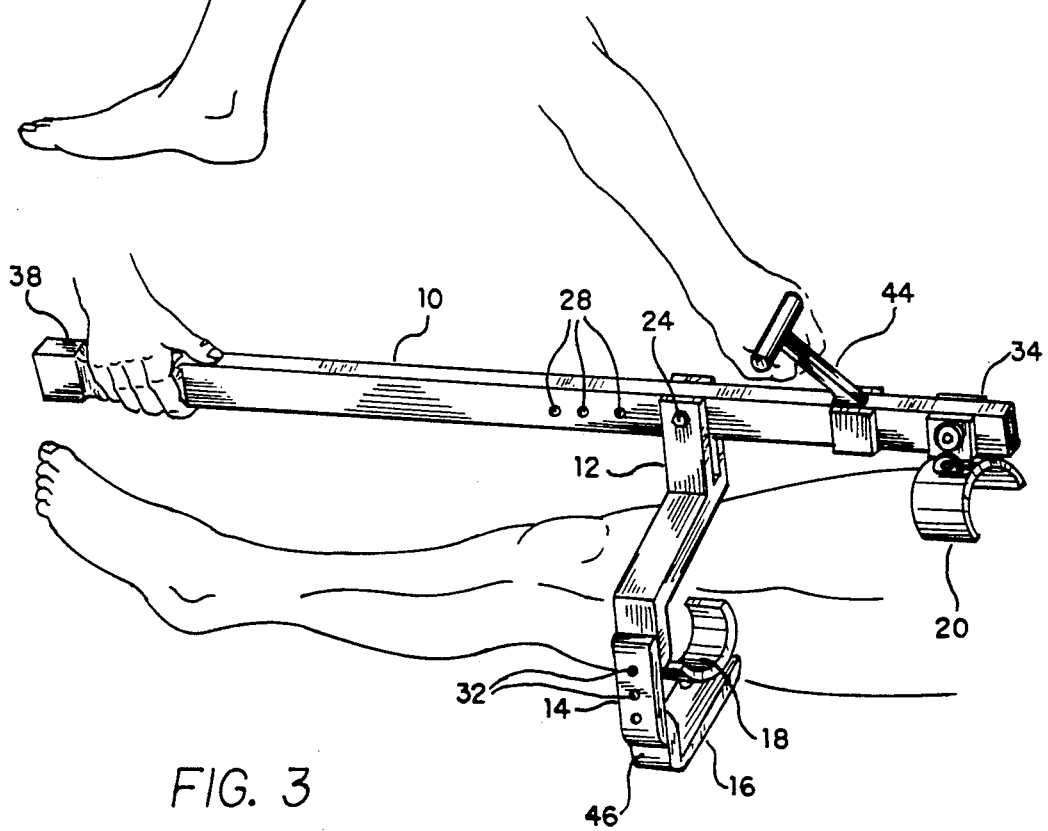
FIG. 3 is a perspective view showing modification of the lever for aligning bones.

FIG. 3 shows a modification of the device shown in FIGS. 1 and 2, in that a leverage grip 44 is provided on lever 10. In this arrangement the user grasps handle 38 and leverage grip 44 to achieve the rotation of lever 10 in the same manner as in FIG. 2.

while it will be apparent that the preferred embodiments of the invention herein disclosed are well calculated to fulfill the objects above-stated, it will be appreciated that the invention is susceptible to modification, variations and change without departing from the proper scope or fair meaning of the subjoined claims.

I claim:

1. A fracture alignment device comprising:
   a lever means having a n outer limb clamp support means pivotally mounted thereon intermediate the ends of said lever means;
   an outer limb clamp means pivotally mounted on said outer limb clamp support means;
   an inner limb clamp means pivotally mounted at one end of said lever means; and
   a handle means provided at a second end of said lever means; whereby
   said lever means may be manually rotated as a second class lever to align bone fractures of large bones.

2. A fracture alignment device as in claim 1 wherein the device is formed of radiolucent materials, whereby the alignment of bone fractures may be monitored by the user.

3. A fracture alignment device as in claim 1 wherein the device is both autoclavable and radiolucent.

4. A fracture alignment device as in claim 1, further comprising adjustment means in both the lever means and the outer limb clamp support means, whereby the outer limb clamp means is adjustable both parallel to and transversely of the lever means, to thereby adjust the device to different size limbs.

5. A fracture alignment device as in claim 1, further comprising:
   a plurality of adjustment holes in said lever means;
   said outer limb clamp support means comprising a bracket pivotally supported by a pivot bolt in one of said plurality of adjustment holes in said lever means, a bracket arm integral with but offset from said bracket, said bracket arm including a plurality of adjustment holes therein, an L-shaped clamp support adjustably mounted on said bracket arm by means of a bolt in one of said plurality of adjustment holes in said bracket arm, said L-shaped clamp support having hinge means thereon for pivotally supporting said outer limb clamp means; and
   an inner limb clamp bracket mounted at said one end of said lever means, said inner limb clamp bracket having hinge means thereon for pivotally mounting said inner limb clamp means.

6. A fracture alignment device as in claim 1, further comprising a leverage grip means mounted on said lever means between said outer limb clamp support means and said one end of said lever means, said leverage grip means enabling the lever means to be firmly grasped and rotated.

* * * * *